US011478522B2

(12) United States Patent
Bomstein et al.

(10) Patent No.: US 11,478,522 B2
(45) Date of Patent: Oct. 25, 2022

(54) SYNERGISTIC HERBAL COMPOSITIONS WITH PREBIOTIC PROPERTIES FOR TREATMENT OF ACNE

(71) Applicant: KAMEDIS LTD., Tel-Aviv (IL)

(72) Inventors: Yonit Bomstein, Petach Tikva (IL); Jonathan Marder, Rechovot (IL)

(73) Assignee: KAMEDIS LTD, Tel Aviv (IL)

( * ) Notice: Subject to any disclaimer, the term of this patent is extended or adjusted under 35 U.S.C. 154(b) by 245 days.

(21) Appl. No.: 16/347,679

(22) PCT Filed: Nov. 13, 2017

(86) PCT No.: PCT/IL2017/051231
§ 371 (c)(1),
(2) Date: May 6, 2019

(87) PCT Pub. No.: WO2018/087766
PCT Pub. Date: May 17, 2018

(65) Prior Publication Data
US 2019/0269747 A1 Sep. 5, 2019

Related U.S. Application Data

(60) Provisional application No. 62/512,090, filed on May 29, 2017, provisional application No. 62/421,297, filed on Nov. 13, 2016.

(51) Int. Cl.
A61K 36/756 (2006.01)
A61P 17/10 (2006.01)
A61P 31/04 (2006.01)
A61P 29/00 (2006.01)
A61K 9/00 (2006.01)
A61K 9/06 (2006.01)
A61K 31/60 (2006.01)
A61K 36/15 (2006.01)
A61K 36/287 (2006.01)
A61K 36/36 (2006.01)
A61K 36/539 (2006.01)
A61K 36/54 (2006.01)
A61K 36/708 (2006.01)
A61K 36/739 (2006.01)
A61P 17/00 (2006.01)
A61K 36/185 (2006.01)

(52) U.S. Cl.
CPC .......... A61K 36/756 (2013.01); A61K 9/0014 (2013.01); A61K 9/06 (2013.01); A61K 31/60 (2013.01); A61K 36/15 (2013.01); A61K 36/185 (2013.01); A61K 36/287 (2013.01); A61K 36/36 (2013.01); A61K 36/539 (2013.01); A61K 36/54 (2013.01); A61K 36/708 (2013.01); A61K 36/739 (2013.01); A61P 17/00 (2018.01); A61P 17/10 (2018.01); A61P 29/00 (2018.01); A61P 31/04 (2018.01)

(58) Field of Classification Search
CPC .... A61K 36/756; A61K 31/60; A61K 36/287; A61P 17/10
See application file for complete search history.

(56) References Cited

U.S. PATENT DOCUMENTS

2013/0323335 A1* 12/2013 Rozenbalt
2014/0107081 A1* 4/2014 Abbott
2014/0134218 A1* 5/2014 Bonner
2014/0271507 A1* 9/2014 Morris-Irvin
2014/0287064 A1* 9/2014 Swenholt
2014/0287076 A1* 9/2014 Xing
2014/3564191 * 9/2014 Gujral

FOREIGN PATENT DOCUMENTS

| CN | 103533947 | 1/2014 | |
| KR | 10-2005-0048299 | 5/2005 | |
| KR | 100772575 | 11/2007 | |
| TW | 201417822 | 5/2014 | |
| WO | WO 2012/090205 | 7/2012 | |
| WO | WO 2014/030155 | 2/2014 | |
| WO | WO 2014/041542 | 3/2014 | |
| WO | WO-2014041542 A2 * | 3/2014 | ............ A61K 36/77 |

OTHER PUBLICATIONS

Kim (Antibacterial Effects of Medicinal Plants from Jeju Island against Acne-inducing Bacteria, J. Appl. Biol. Chem. 50(2), 101-103, 2007). (Year: 2007).*
European Search Repot for EP Application No. 17869864.3 dated May 4, 2020.
Kim Jin-Man et al. "Study on the Anti-microbacterial Activity, Anti-inflammatory and Anti-allergic Effects of Several Herb-Extract", Korean Journal Oriental Physiology & Pathology, vol. 20, No. 1, Feb. 25, 2006, pp. 103-114.
Sunmin Park et al. "Synergistic topical application of salt-processed Phellodendron amurense and Sanguisorba officinalis Linne alleviates atopic dermatitis symptoms by reducing levels of immunoglobulin E and pro-inflammatory cytokines in NC/Nga mice" Molecular Medicine Reports, vol. 12, No. 5, Nov. 22, 2015, pp. 7657-7664.

(Continued)

Primary Examiner — Susan Hoffman
Assistant Examiner — Jacob A Boeckelman
(74) Attorney, Agent, or Firm — Pearl Cohen Zedek Latzer Baratz LLP

(57) ABSTRACT

Disclosed is a topical formulation comprising the herbal extracts *Portulaca oleracea* extract, *Rheum palmatum* root extract, *Chrysanthemum indicum* flower extract, *Scutellaria baicalensis* root extract *Phellodendron amurense* bark extract and *Sanguisorba officinalis* root extract or their active molecules. Disclosed also is a topical formulation comprising *Portulaca oleracea* extract, *Rheum palmatum* root extract, *Chrysanthemum indicum* flower extract, *Scutellaria baicalensis* root extract and *Phellodendron amurense* bark extract or their active molecules. Further disclosed are methods of treating or preventing acne, comprising administering the disclosed formulations.

20 Claims, 7 Drawing Sheets

(56) References Cited

OTHER PUBLICATIONS

Choi H R et al., "External composition comprising herbal extracts capable of improving skin keratosis and inflammation and alleviating itchness" vol. 2008, No. 14, Aug. 7, 2007.
International Search Report for PCT Application No. PCT/IL2017/051231, dated Mar. 7, 2017.
He Yongheng; Medical Cases of Masters for Anorectal Diseases and Masterly Analysis Thereof; People's Military Doctor Press; Jan. 31, 2007.
Tian Yan; Manual for Treatment of Common Diseases with Medicinal Liquors ; Jindun Press ; Mar. 31, 2015.
Chaudhary, Shahid Shah et al. "The In vitro anti-acne activity of two unani drugs." Ancient science of life vol. 33,1 (Jul. 2013): 35-8.
Pharmacology and Clinics of Traditional Chinese Medicine for Dermatosis, Chen Mingling et al., pp. 143-146, China Science and Technology Press, Edition I in Oct. 2017.
Atlas and Formulations of Common Traditional Herbal Medicine 4, Yang Weiping et al., p. 194, Guizhou Science and Technology Press, Edition I in Sep. 2012.
Pharmacology and Clinics of Modern Chinese Medicine, Wang Benxiang, p. 594, Tianjin Science & Technology Translation & Publishing Co., Ltd, edition I in Jun. 2004.
Modern Cosmetic Science and Technology II, Qiu Binyi et al., p. 1504, China Light Industry press, edition I in Mar. 2016.
Office Action and Search Report dated Apr. 9, 2021 for corresponding Chinese Application No. 2017800746790.
Office Action dated May 9, 2021 for corresponding Israeli Application No. 266441.
Seongdae Kim et al.; In Vitro Antioxidant and Anti-Propionibacterium acnes Activities of ColdWater, Hot Water,and Methanol Extracts, and Their Respective Ethyl Acetate Fractions, from *Sanguisorba officinalis* L. Roots; Molecules 2018, vol. 23, No. 11.
Hanna-Leena Kelhälä, et al.; IL-17/Th17 Pathway Is Activated in Acne Lesions; PLoS One; Aug. 2014, vol. 9, Issue 8.
George W. Agak, et al.; Propionibacterium acnes induces an interleukin-17 response in acne vulgaris that is regulated by vitamin A and vitamin D; J Invest Dermatol., Feb. 2014 32(2), 366-377.
Liang-Yu Wu et al., "Analysis of chemical composition of *Chrysanthemum indicum* flowers by GC/MS and HPLC", *WPI/Thomson, Journal of Medicinal Plants Research* vol. 4(5), pp. 421-426, Mar. 4, 2010 (Mar. 4, 2010).
Office Action dated Feb. 7, 2022 for corresponding Canadian Application No. 3,060,305.
Kaewklom, Siriporn et al. "Structural and biological features of a novel plant defensin from Brugmansia x candida." PloS one vol. 13,8 e0201668. Aug. 2, 2018, https://doi.org/10.1371/journal.pone.0201668.

\* cited by examiner

SYNERGISTIC HERBAL COMPOSITIONS WITH PREBIOTIC PROPERTIES FOR TREATMENT OF ACNE

CROSS-REFERENCE TO RELATED APPLICATIONS

This application is a U.S. national stage of International Application No. PCT/IL2017/051231, International Filing Date Nov. 13, 2017, which claims the benefit of U.S. Provisional Application No. 62/421,297, filed Nov. 13, 2016, and U.S. Provisional Application No. 62/512,090, filed May 29, 2017, all of which are hereby incorporated by reference.

FIELD OF THE INVENTION

The invention is directed to topical formulations comprising different mixtures of plant extracts together with additional ingredients. The invention is further directed to use of the formulations in treating acne.

BACKGROUND OF THE INVENTION

Acne vulgaris (cystic acne or "acne") is a common human skin disease, characterized by areas of skin with redness, comedones (blackheads and whiteheads), papules (pinheads), pustules (pimples), nodules (large papules) and possibly scarring. Acne affects mostly skin with the densest population of sebaceous follicles; these areas include the face, the upper part of the chest, and the back. Severe acne is inflammatory, but acne can also manifest in noninflammatory forms. The lesions are caused by changes in pilosebaceous units, skin structures consisting of a hair follicle and its associated sebaceous gland, changes that require androgen stimulation. Acne occurs most commonly during adolescence, and often continues into adulthood.

In light of the disadvantages of known treatments for acne, there is a need for a topical composition comprising herbs for the treatment thereof.

SUMMARY OF THE INVENTION

According to some embodiments of the invention, there is provided a topical formulation comprising *Portulaca oleracea* extract, *Rheum palmatum* root extract, *Chrysanthemum indicum* flower extract, *Scutellaria baicalensis* root extract, *Phellodendron amurense* bark extract and *Sanguisorba officinalis* root extract or their active molecules.

According to some embodiments of the invention, the topical formulation is for use in treating or preventing acne.

According to some embodiments of the invention, the formulation further comprises *Cinnamomum zeylanicum* bark extract, *Picea abies* extract, glycerin, or any combination thereof.

According to some embodiments of the invention, the formulation comprises salicylic acid which may be in the range of 0.1-5.0% w/w.

According to some embodiments of the invention, the formulation is in a form of a gel.

According to some embodiments of the invention, there is provided a method of treating acne comprising the step of topically applying the composition of the invention to a subject in need.

Embodiments of the invention are directed to a topical formulation comprising the herbal extracts *Portulaca oleracea* extract, *Rheum palmatum* root extract, *Chrysanthemum indicum* flower extract, *Scutellaria baicalensis* root extract *Phellodendron amurense* bark extract and *Sanguisorba officinalis* root extract or their active molecules. Further embodiments are directed to the use of such a formulation, as detailed herein, in treating or preventing acne.

According to some embodiments, the topical formulation comprises an anti-inflammatory compound, anti-microbial agent, prebiotic ingredient, skin hydration enhancing ingredient, analgesic agent, anti-oxidant, a sebum regulator, a keratolytic agent or any combination thereof.

According to some embodiments, the topical formulation further comprises *Cinnamomum zeylanicum* bark extract, *Picea abies* extract, glycerin, or any combination thereof. According to some embodiments, the topical formulation further comprises salicylic acid. According to some embodiments, the amount of the salicylic acid in the topical formulation is in the range of 0.1-5.0% w/w.

According to some embodiments, the topical formulation is a gel. According to some embodiments, the topical formulation has a pH in the range of 4.0-5.5.

According to some embodiments, the combined concentration of the herbal extracts in the topical formulation is at least 1% w/w. According to some embodiments, the topical formulation comprises about total of 5.5% w/w extracts of *Chrysanthemum indicum* flower, *Portulaca oleracea*, *Rheum palmatum* root, and *Scutellaria baicalensis* root; about 3% w/w *Sanguisorba officinalis* root and about 3% w/w *Phellodendron amurense* bark. According to some embodiments, the topical formulation comprises about 1.5% w/w *Chrysanthemum indicum* flower extract, about 1.5% w/w *Portulaca oleracea* extract, about 1.5% w/w *Rheum palmatum* root extract, and about 1.0% w/w *Scutellaria baicalensis* root extract.

Further embodiments are directed to a method of treating acne comprising the step of topically applying the topical composition disclosed herein.

Further embodiments are directed to a topical formulation comprising *Portulaca oleracea* extract, *Rheum palmatum* root extract, *Chrysanthemum indicum* flower extract, *Scutellaria baicalensis* root extract and *Phellodendron amurense* bark extract or their active molecules.

DESCRIPTION OF THE DETAILED EMBODIMENTS OF THE INVENTION

Figure 1:
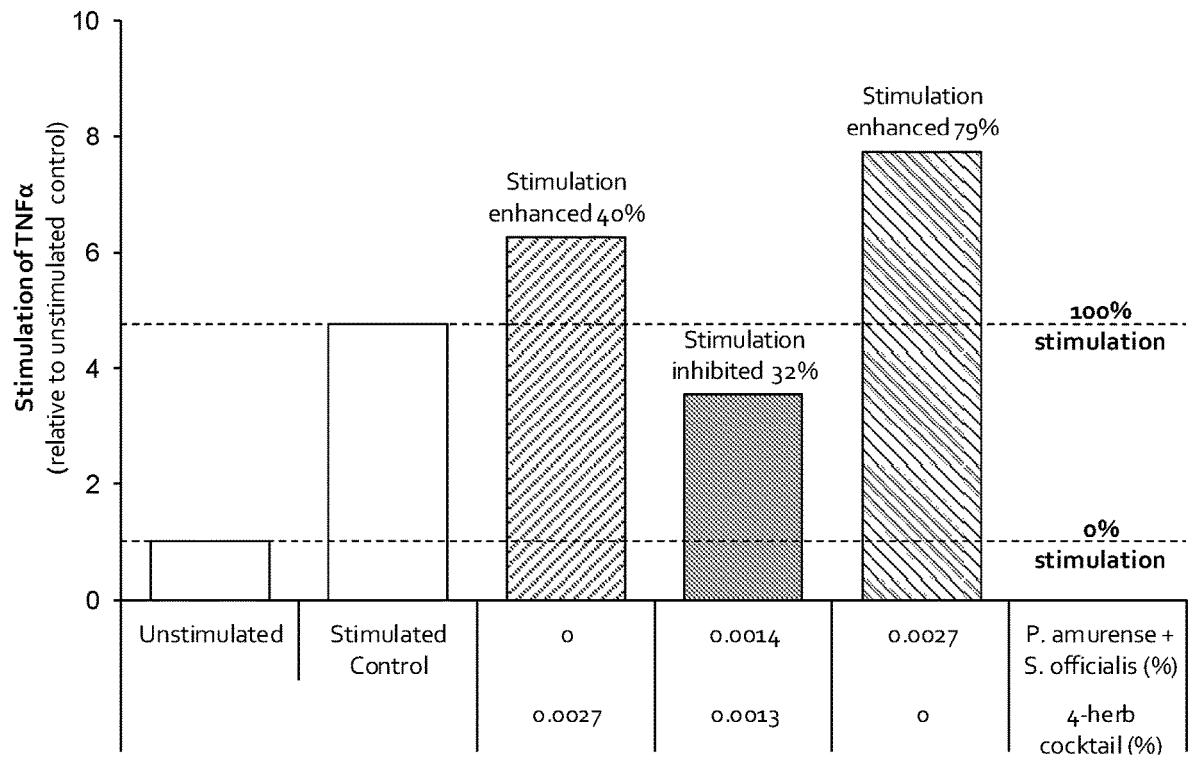
FIG. 1 presents results of various compositions on the secretion of TNF-alpha from keratinocytes stimulated with EGF/LPS (Epidermal Growth Factor/Lipopolysaccharide)

One embodiment of the invention is a topical formulation comprising *Portulaca oleracea* extract, *Rheum palmatum* root extract, *Chrysanthemum indicum* flower extract *Scutellaria baicalensis* root extract, *Phellodendron amurense* bark extract and *Sanguisorba officinalis* root extract or their active ingredients, as detailed below for use in treating acne.

According to some embodiments, the topical formulation further comprises salicylic acid, *Cinnamomum zeylanicum* bark extract, *Picea abies* extract, glycerin, or any combination thereof.

List of Several Active Ingredients in the Extracts

| Herb | Markers |
| --- | --- |
| *Scutellaria baicalensis* | Baicalin |
| *Chrysanthemum indicum* | Buddleoside |
| *Sanguisorba officinalis* | Gallic acid |
| *Portulaca oleracea* | Flavonoids |
| *Rheum palmatum* | Rhein |
| *Phellodendron amurense* | Berberine |

According to some embodiments, the topical formulation includes one or more of anti-inflammatory ingredient, sebum regulation ingredient, anti-microbial ingredient, prebiotic ingredient, skin hydration enhancing ingredient, analgesic agent, keratolytic ingredient, anti-oxidant and any combination thereof.

According to some embodiments, the active ingredients in the topical formulation described herein provide a synergistic effect in treating acne. According to further embodiments, the combination of at least two or more of *Rheum palmatum* root extract, *Portulaca oleracea* extract, *Chrysanthemum Indicum* flower extract, *Scutellaria baicalensis* root extract, *Phellodendron amurense* bark extract and *Sanguisorba officinalis* root extract or their active ingredients in the formulation provide a synergistic effect in treating acne. The synergistic/complementary effect may be in treating the condition by enhancing anti-inflammatory activity, by prebiotic effect, by antibiotic effect, by enhancing the penetration of the active ingredients into the skin, by lowering skin irritation, or any combination thereof.

*Rheum palmatum* root extract, *Scutellaria baicalensis* root extract, *Phellodendron amurense* bark extract, *Sanguisorba officinalis* root extract or their actives as well as *Cinnamomum zeylanicum* bark extract may act by exhibiting anti-bacterial, especially anti-*P. acne*, activity, which is beneficial for treating acne blemishes.

*Chrysanthemum indicum* flower extract and *Rheum palmatum* root extract or their actives may act synergistically by exhibiting prebiotic activity, especially pro-*S. epidermidis* activity, which is beneficial for balancing natural microbiota of the skin and therefore, treating acne blemishes.

Sebum production is increased by excess of testosterone during puberty. Free testosterone (androgene) penetrates the sebaceous cell and is transformed to dihydrotestosterone (DTH) mediated by 5 alpha reductase. *Scutellaria baicalensis* and *Rheum palmatum* decrease androgen receptor expression and therefore, may be used to decrease androgen mediated stimulation of sebaceous gland activity, resulting in decreased sebum production. *Cinnamomum zeylanicum* bark extract regulates sebum production by anti-5 alpha-reductase action. Thus, the combination of the *Rheum palmatum* and *Scutellaria baicalensis* root extracts, or their active ingredients thereof, together with *Cinnamomum zeylanicum* bark extract (Sepicontrol A5) or any other equivalent ingredients, possibly synergistically, reduces sebum secretion and absorption of oils from the skin.

Salicylic acid is a keratolytic agent that is widely used in topical acne preparations. It might enhance the penetration of other herbal active components.

*Rheum palmatum* root extract, *Scutellaria baicalensis* root extract, *Phellodendron amurense* bark extract, *Sanguisorba officinalis* root extract as well as *Cinnamomum zeylanicum* bark extract and *Picea abies* extract have antioxidative properties. Therefore, the combination thereof, or of any other equivalent ingredient, enhances, possibly synergistically, the antioxidant activity of the herbal extracts, thus reducing acne severity and symptoms.

According to further embodiments, the topical formulation comprises salicylic acid. According to further embodiments, the topical formulation comprises at least 0.1% w/w salicylic acid. According to further embodiments, the topical formulation comprises at least 1.0% w/w salicylic acid. According to further embodiments, the topical formulation comprises at least 1.5% w/w salicylic acid. According to further embodiments, the topical formulation comprises salicylic acid in the range of 0.1-5.0% w/w. According to further embodiments, the topical formulation comprises salicylic acid in the range of 1-3% w/w. According to further embodiments, the topical formulation comprises salicylic acid in the range of 1.5-2.5% w/w. According to further embodiments, the topical formulation comprises about 2% salicylic acid.

According to some embodiments, the pH of the topical formulation is between about 3.0-6.0. According to further embodiments, the pH of the topical formulation is between about 3.5-5.0. According to further embodiments, the pH of the topical formulation is between about 4.5-5.0.

According to some embodiments, the combined concentration of the herbal extracts in the formulation is at least 1%. According to some embodiments, the combined concentration of the herbal extracts in the formulation is at least 2.5%. According to some embodiments, the combined concentration of the herbal extracts in the formulation is at least 5%. According to some embodiments, the combined concentration of the herbal extracts in the formulation is at least 7.5%. According to some embodiments, the combined concentration of the herbal extracts in the formulation is between 10-12.5%. According to some embodiments, the combined concentration of the herbal extracts in the formulation is 11.5%.

Using routine methods, the formulations of the present invention may be formulated into a variety of preparations, depending on the intended use. These preparations include, but are not limited to, topical skin compositions for medical use and topical skin cosmetic compositions.

As topical skin compositions for medical use and topical skin cosmetic compositions, many forms of gels, ointments, soaps, creams and lotions may be used. The formulation may be applied in any suitable manner, i.e., by hand, spatula, spray or pad.

The formulation of the invention may be in the form of a cream. The formulation of the invention may be applied to the entire area of the skin affected by the acne or locally to each sore. The formulations of the invention show high dermal compatibility and low irritation behavior when applied to human skin. According to some embodiments, the formulations are applied to the body and subsequently remove therefrom, e.g., by washing with water.

When the topical compositions of the present invention are used as cosmetic compositions, cosmetic or dermatological acceptable ingredients may be optionally incorporated in arbitrary combinations as desired and determined in accordance by a person skilled in the art. According to some embodiments, the compositions may include oils, fats, waxes, detergents, conditioners, pH modifiers, preservatives, solvents, viscosity modifiers, colorants, perfumes, dyestuffs and the like.

The composition may be in a form of oil-in-water, water-in-oil, water-in-oil-in-water, and oil-in-water-in-silicone emulsions, a cream, an ointment, an aqueous solution, a lotion, a soap, a paste, a foam, an emulsion, a gel, a salve, an oil, a wash, a conditioner or an aerosol.

According to an embodiment of the invention, the compositions of the invention are administered once a day. According to other embodiments, the compositions are administered twice a day, three times a day or more.

According to some embodiments of the invention, the composition is administered for about 1 day, 10 days or more, 20 days, 30 days, 60 days, 90, 120 days or more.

In some embodiments of the invention, the composition further comprises cleaning agents or detergents that are typically anionic, cationic, non-ionic or amphoteric surfactants. Typical anionic surfactants are carboxylates, sulfonates, sulfates or phosphates, e.g. fatty-acid soaps, salts of lauryl sulfate and salts of lauryl ether sulfate. Examples of cationic surfactants are aliphatic mono-, di- and poly-amines derived from fatty and rosin acids, amine oxides, ethoxylated alkyl amines and imidazolines. Examples of non-ionic surfactants are polyoxyethylene surfactants, alkylphenol ethoxylates, carboxylic acid esters, e.g., mono and diglycerides, polyoxyethylene esters and fatty acid diethanolamine condensates. Amphoteric surfactants are those containing combinations of the anionic and cationic groups described above, particularly those containing both acid carboxyls and basic nitrogen groups. Typical amphoteric surfactants are imidazolines and betaines, e.g., lauric and myristic imidazolines and betaines, and amidopropyl-betaines.

The topical pharmaceutical compositions may also comprise a suitable emulsifier which refers to an agent that enhances or facilitates mixing and suspending oil-in-water or water-in-oil. The emulsifying agent used herein may consist of a single emulsifying agent or may be a nonionic, anionic, cationic or amphoteric surfactant or blend of two or more such surfactants; preferred for use herein are nonionic or anionic emulsifiers. Such surface-active agents are described in "McCutcheon's Detergent and Emulsifiers," North American Edition, 1980 Annual published by the McCutcheon Division, MC Publishing Company, 175 Rock Road, Glen Rock, N.J. 07452, USA.

The CTFA Cosmetic Ingredient Handbook, Second Edition (1992) describes a wide variety of non-limiting cosmetic ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch-hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizate), skin treating agents, thickeners, and vitamins and derivatives thereof.

Other dermatological disorders which may be treated or prevented by embodiments of the formulation are for example, without being limited folliculitis and oily skin conditions The term "about" refers to ±10%. The term % w/w, relates to the weight of a particular ingredient as a percent of the weight of the entire formulation.

The expression "dermatologically acceptable carrier" as used herein, means a carrier that is compatible with the skin, scalp, hair, nail and the like.

The term "preventing" refers to keeping a disease, disorder or condition from occurring in a subject. In some cases the subject may be at risk for developing the disease, but has not yet been diagnosed as having the disease. In some instances, the term "preventing" refers to preventing the next cycle of the disease from occurring.

The term "prebiotic" used herein is directed to substances that selectively increase the growth and survival of beneficial microorganisms of the skin flora, e.g., *Staphylococcus epidermidis*, are categorized as "prebiotic". Although various types of prebiotics are known, there is still an increasing need for more-active alternatives or additives that may act in a synergistic manner.

The plant extracts used herein may be purified by the use of a polar solvent (i.e. polar extract) such as, ethyl alcohol (ethanol), butyl alcohol (butanol), methanol, water or propanol, propylene glycol, butylene glycol, glycerin. The polar extracts of the present invention may comprise any percentage of a polar solvent.

Alternatively, the plant extracts may be purified by the use of a non-polar solvent (i.e. non-polar extract) such as, without being limited to, isooctane. The non-polar extracts of the present invention may comprise any percentage of non-polar solvents.

Typically, hydrophobic molecules tend to be non-polar and thus non-polar solvents are used. Hydrophilic molecules tend to be polar and dissolve by water and/or other polar substances.

The active ingredients can be concentrated in the extract via chromatography and the like.

Typically, the plant extract of the present invention is an aqueous extract. In order to obtain a purified plant extract (e.g. with reduced levels of organic salts and/or heavy metals and/or starch in the plant extract), the aqueous plant extract is typically further purified by chromatography. Glycerin or propylene glycol might be added to the water extracts to elevate the solubility of the extract, to elevate the penetration ability into the skin and to further preserve the extract. The extracts might contain also a preservative system.

Thus, according to another embodiment, there is provided a method of preparing a composition comprising concentrated herbal extracts for treating and/or preventing acne, the method comprising: (a) subjecting a plant to ×1-10 volumes of water to produce an extract of the plant; and (b) reducing the amount of organic salts and/or heavy metals and/or starch in the plant extract using a macroporous resin that results in an elevated content of the active ingredients present in the plant extract.

According to some embodiments, the formulation comprises any additional ingredients, including solvents, emollients, moisturizers, conditioners, viscosity builders, skin calmers, emulsifiers, pH adjusters, preservatives, antioxidants, viscosity increasing agents, perfumes, humectants, anti-acne agents, stabilizers and detergents.

Some embodiments of the invention are directed to the synergistic biological activity between *Portulaca oleracea* extract, *Rheum palmatum* root extract, *Chrysanthemum indicum* flower extract, *Scutellaria baicalensis* root extract and a mixture of *Phellodendron amurense* bark and *Sanguisorba officinalis* root extracts for inhibiting IL-8. Some embodiments of the invention are directed to the synergistic biological activity between *Portulaca oleracea* extract, *Rheum palmatum* root extract, *Chrysanthemum indicum* flower extract, *Scutellaria baicalensis* root extract and *Phellodendron amurense* bark extracts for inhibiting IL-1a. Some embodiments of the invention are directed to the synergistic effect was shown between *Portulaca oleracea* extract, *Rheum palmatum* root extract, *Chrysanthemum indicum* flower extract, *Scutellaria baicalensis* root and *Phellodendron amurense* bark extracts. Thus, according to some embodiments, the composition comprises *Portulaca oleracea* extract, *Rheum palmatum* root extract, *Chrysanthemum indicum* flower extract, *Scutellaria baicalensis* root, *Phellodendron amurense* bark and *Sanguisorba officinalis* root extarcts. According to some embodiments, the composition comprises *Portulaca oleracea* extract, *Rheum palmatum* root extract, *Chrysanthemum indicum* flower extract, *Scutellaria baicalensis* root and *Phellodendron amurense* bark extracts.

Some embodiments are directed to an antimicrobial composition, effective against *Propionibacterium acnes*, wherein the composition comprises any one of *Portulaca oleracea* extract, *Rheum palmatum* root extract, *Chrysanthemum indicum* flower extract, *Scutellaria baicalensis* root extract, *Phellodendron amurense* bark extract and *Sanguisorba officinalis* root extract or any combination thereof.

Some embodiments are directed to a prebiotic and/or antibiotic composition comprising any combination of any of the herbal extracts disclosed herein, e.g., *Rheum palmatum* root, *Portulaca oleracea, Chrysanthemum indicum* flower, *Scutellaria baicalensis* root, *Phellodendron amurense* bark and/or *Sanguisorba officinalis* root extracts.

Some embodiments of the invention are directed to the synergistic/complementary effect shown between *Phellodendron amurense* bark extract and *Chrysanthemum indicum* flower extract.

According to some embodiments, the topical formulation comprises a total of about 5.5% extracts of *Chrysanthemum indicum* flower, *Portulaca oleracea, Rheum palmatum* root, and *Scutellaria baicalensis* root. According to some embodiments, the topical formulation comprises a total of about 5.5% extracts of *Chrysanthemum indicum* flower, *Portulaca oleracea, Rheum palmatum* root, and *Scutellaria baicalensis* root together with about 3% w/w *Sanguisorba officinalis* root extract and about 3% w/w *Phellodendron amurense* bark extract. According to some embodiments, the topical formulation comprises about 1.5% w/w *Chrysanthemum indicum* flower extract, about 1.5% w/w *Portulaca oleracea* extract, about 1.5% w/w *Rheum palmatum* root extract, and about 1.0% w/w *Scutellaria baicalensis* root extract, possibly together with about 3% w/w *Sanguisorba officinalis* root extract and about 3% w/w *Phellodendron amurense* bark extract.

EXAMPLES

Example 1

Assessment of Synergistic Anti-Inflammatory Effect of Herbal Extracts in Keratinocytes and in Natural and Artificial Human Skin Models Acne lesions are characterized by high content of pro-inflammatory cytokines such as tumor necrosis factor alpha (TNF-α), interleukin-8 (IL-8) and interleukin-1 (IL-1). The increase in their activity precedes hyperkeratinization of follicles in inflammatory acne.

The acne spot treatment, related to herein includes the use of a product (Kamedis) containing four herbal extracts: *Portulaca oleracea* extract, *Rheum palmatum* root extract, *Chrysanthemum indicum* flower extract, *Scutellaria baicalensis* root extract. The synergistic effect between the above mixture or four extract together with two additional herbal extracts, i.e., *Phellodendron amurense* bark extract and/or *Sanguisorba officinalis* root extract, have been examined as follows and the results thereof are presented below.

Materials and Experimental Procedures

Cell Culture Model

Toxic levels of herbal extracts on human keranocyte cell line HaCaT stimulated EGF (Epidermal Growth Factor) and LPS (Lipopolysaccharide) have been predetermined by vital staining with MTT (3-(4,5-Dimethylthiazol-2-yl)-2,5-Diphenyltetrazolium Bromide).

HaCaT cells with 70% confluence were exposed to stimulation with EGF/LPS and to test items at non-toxic doses for 24 hours. Dexamethasone was used as a positive control. TNF-alpha secretion from the stimulated cells was determined by commercial ELISA (Enzyme-Linked Immunosorbent Assay) kit.

Skin Models

Samples of human natural skin (from healthy patients undergoing plastic surgery) or artificial, 3D human reconstructed skin (EpiDerm™ System; Mattek) were exposed to stimulation with LPS or phorbol 12-myristate 13-acetate (PMA), respectively. Combinations of herb extracts were applied in an ointment matrix that was spread onto the skin-sample surface and incubated for 48 hours (human skin) or for 6 hours (EpiDerm™ System). Viability of the skins was measured by the MTT assay. Dexamethasone was used as a positive control. IL-1a and IL-8 secreted from the stimulated cells were quantified using commercial ELISA kits.

Calculation of Results (all Models)

Cytokine secretion values were all calculated as stimulation ratios, i.e. relative to the secretion value for unstimulated control. "Inhibitions of stimulation" were calculated from the stimulation values according to Equation 1:

$$\left(\frac{\text{stimulated control} - \text{sample}}{\text{stimulated control} - 1} \times 100\%\right) \quad \text{Equation 1}$$

Results

Human Keratinocyte Model

FIG. 1 presents the EGF/LPS stimulation of the TNF-alpha release relative to the stimulated non-treated cells (negative control), wherein the negative control was defined as the point of 0% stimulation. One treatment included 0.027% of 4-herb cocktail comprised of *Portulaca oleracea, Rheum palmatum* root, *Chrysanthemum indicum* flower, and *Scutellaria baicalensis* root extracts, diluted in the growth medium. A second treatment included 0.027% of *Phellodendron amurense* bark and *Sanguisorba officinalis* root extracts. A third treatment consisted of all six herbal extracts at approximately half the aforementioned concentrations. The geometric standard deviation between replicates in FIG. 1 is 30%.

Suppression of TNF-alpha release from stimulated keratinocytes, shown in FIG. 1, was achieved using a cocktail of all six herbal extracts In contrast, TNF-alpha release was actually increased (negative inhibition) by partial mixtures consisting of only some extracts. Thus, a highly-desired synergistic effect is apparent when combining the six extracts. It is noted that the model tested is relevant to acne.

Natural Human Skin Model

Figure 2:
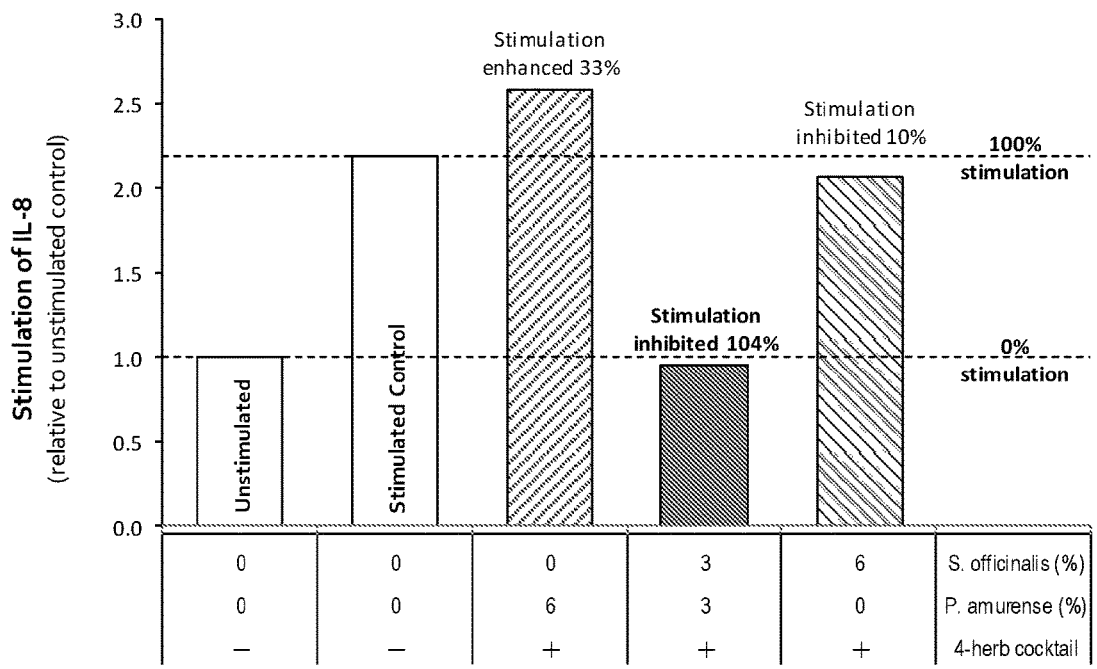
FIG. 2 presents results obtained using various compositions regarding the IL-8 release from human skin stimulated with LPS.

FIG. 2 illustrates results obtained for stimulation of human skin with LPS. Particularly, FIG. 2 presents the secretions of IL-8 from natural skin, wherein inhibition above 85% is considered to be statistically significant at the α=0.05 level (Tukey HSD).

As shown in FIG. 2, LPS induced a 2.2-fold increase in the secretion of IL-8 from skin into the assay media. In LPS-activated samples treated with a four-herbal cocktail (extracts of *Portulaca oleracea, Rheum palmatum* root, *Chrysanthemum indicum* flower, *Scutellaria baicalensis* root) and a formulation containing either 6% *Phellodendron amurense* bark extract or 6% *Sanguisorba officinalis* root extract, no inhibition of IL-8 secretion was observed. However, stimulation of IL-8 secretion was completely inhibited by a formulation containing all six herbal extracts. Thus, a synergistic effect between the *Phellodendron amurense* and *Sanguisorba officinalis* extracts is apparent.

It is noted that the model tested here is relevant to acne.

Artificial Human Skin (EpiDerm™ System) Model

In experiments to measure secretions of IL-1α and IL-8 from artificial skin, PMA induced 2.9-fold and 2.6-fold stimulations, respectively, in release of the two cytokines into the assay medium.

Figure 3:
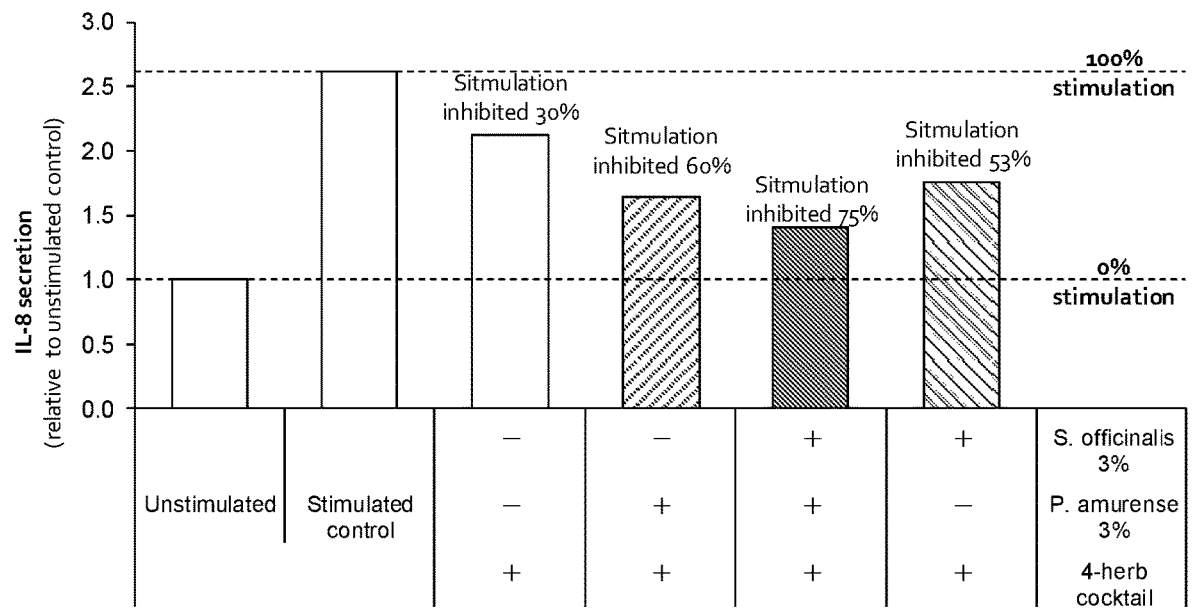
FIG. 3 presents the results obtained using various compositions, regarding the secretion of IL-8 from artificial skin stimulated with phorbol 12-myristate 13-acetate (PMA)

Particularly, the results for IL-8 secretion from artificial skin are presented in FIG. 3, which illustrates that the application of a composition of four herbal extracts [*Chrysanthemum indicum* flower (1.5%), *Portulaca oleracea* (1.5%), *Rheum palmatum* root (1.5%) and *Scutellaria baicalensis* root (1%), related to in FIG. 3 as "4-herb cocktail"] provided 60% or 53% of stimulation inhibition, when administered together with each of extracts 3% *Sanguisorba officinalis* root or 3% *Phellodendron amurense* bark, respectively. Moreover, when all six extracts were administered together, the inhibition of stimulation rose to 75%, a statistically significant result that indicates synergism between the six elements of the composition.

It is noted that the test model is relevant to acne.

Figure 4:
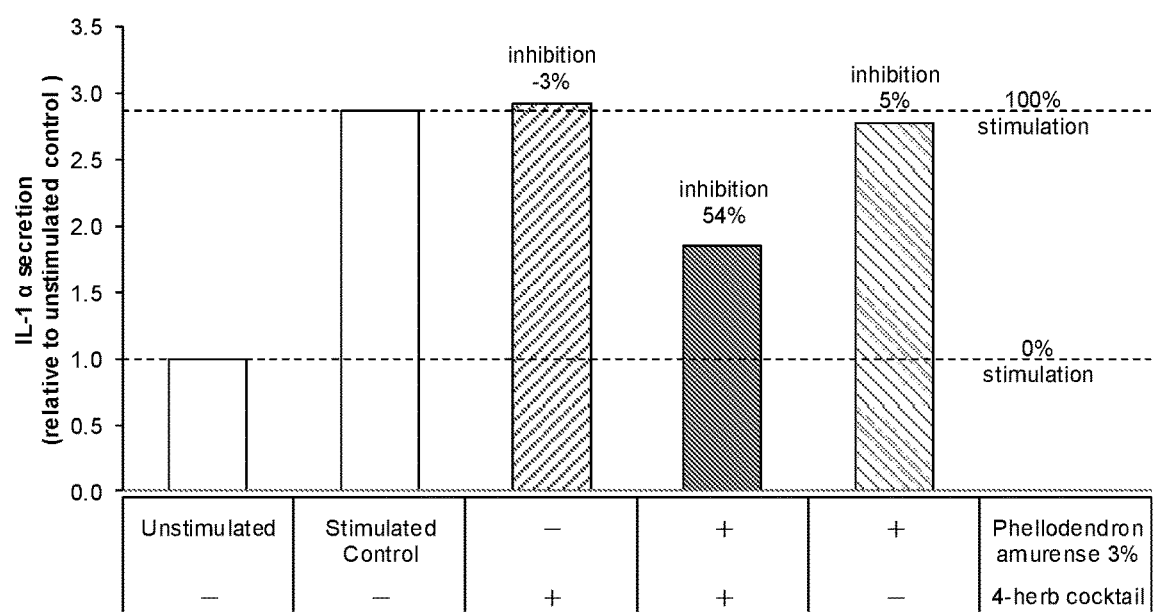
FIG. 4 presents the results obtained using various compositions, regarding the secretion of IL-1a from artificial skin stimulated with PMA.

The results for IL-1a secretion from an artificial skin model are presented in FIG. 4, where the values obtained are shown relative to the unstimulated control. In this experiment, inhibitions greater than 44% are considered significant at the α=0.05 level (Tukey HSD). As shown in FIG. 4, only one combination of five herbal extracts [*Chrysanthemum indicum* flower (1.5%), *Portulaca oleracea* (1.5%), *Rheum palmatum* root (1.5%) and *Scutellaria baicalensis* root (1%)] together with 3% *Phellodendron amurense* bark provided significant inhibition. The cocktail of four herbal extracts [*Chrysanthemum indicum* flower (1.5%), *Portulaca oleracea* (1.5%), *Rheum palmatum* root (1.5%) and *Scutellaria baicalensis* root (1%)] showed no sign of any inhibitory activity against IL-1α secretion. Application of *Phellodendron amurense* bark extract was also without noticeable effect. Thus, the significant inhibition of IL-1α secretion observed using the above five herbal extracts appears to indicate a synergy between the first four (or at least part of the first four) and the *Phellodendron amurense* bark extract.

Summary

Synergetic biological activity was observed between four herbal extracts (*Portulaca oleracea* extract, *Rheum palmatum* root extract, *Chrysanthemum indicum* flower extract, *Scutellaria baicalensis* root extract) and a mixture of *Phellodendron amurense* bark and *Sanguisorba officinalis* root extracts (altogether six herbal extracts) for inhibiting IL-8, whereas for inhibiting IL-1α, a synergistic effect was shown between the above four herbal extracts and *Phellodendron amurense* (five herbal extracts altogether).

Example 2

Assessment of Prebiotic and Antibiotic Effects of Herbal Extracts

Background

Human skin is living tissue composed of human cells and a diverse microflora that includes fungi, bacteria and viruses. While some of these microorganisms are harmful, many others may benefit their host, e.g., by providing protection against the invasion of more-harmful organisms. It is believed that disrupting the balance in the skin microfloral population may result in disorders or infections.

Microbial involvement is implicated in many common skin disorders. The skin bacterium *Propionibacterium acnes* is associated with the common human skin disease acne vulgaris (cystic acne or "acne"), and *Staphylococcus capitis* was found to have a role in the progression of the acne.

On the other hand, *Staphylococcus epidermidis* is a common skin microorganism that is considered beneficial. Substances that selectively increase the growth and survival of beneficial microorganisms of the skin flora, e.g., *Staphylococcus epidermidis*, are categorized as "prebiotic". Although various types of prebiotics are known, there is still an increasing need for more-active alternatives or additives that may act in a synergistic manner.

Materials and Experimental Procedures

Agar Diffusion Assay

This is a qualitative analysis aimed to determine the ability of an extract to inhibit the growth of pathogens. Cultures of *Propionibacterium acnes* were diluted (1:1,000) in fresh media and plated on soft agar plates, and 3 filter-paper discs were put on each plate. Aliquots of 1004 of each extract were applied to the filter-paper discs. Plates were incubated for 5 days. The samples diffuse into the agar around the well and are assayed for an ability to produce a Zone of inhibition. The diameter of Zones, including the diameter of the well was recorded.

Microplate Dilution Assay

This is a quantitative analysis aimed to determine the inhibitory concentration of each extract against each pathogen in its growth medium. Each plant extract was diluted (a series of 1:2 dilutions) in the appropriate growth media and aliquots of 100 μL were distributed in 10 wells of 96-wells plates. Overnight grown cultures were diluted 1:1000 in fresh media, and 100 μL were added to each well, giving final concentrations of the extracts ranging between 25% and ~0.05%. Controls were extracts without pathogens (to look for contaminations) or pathogens in fresh growth media without the plant extracts (maximal growth). Plates were incubated for 5 days and the minimal concentration at which no growth was observed was determined. This concentration is defined as the MIC (minimal inhibitory concentration).

Bacterial Growth

Staphylococcus epidermidis or Staphylococcus capitis were plated on nutrient broth (NB) agar plates. Overnight bacterial colonies were suspended to an optical density of 0.1 at 600 nm and then were diluted 1:100 in sterile saline. Two-fold serial dilutions of plant extracts were prepared in 96-well plates. The controls were 1) wells with NB medium but without bacteria, 2) wells with extract but without NB medium and 3) wells with both NB medium and extract but without bacteria. Bacterial growth was followed by measuring 600 nm absorbance every 5 minutes during 24 hours incubation at 37° C. In all experiments between two to four independent repetitions were performed.

Results

Anti-P. acne Effect of Herbal Extracts

Figure 5:
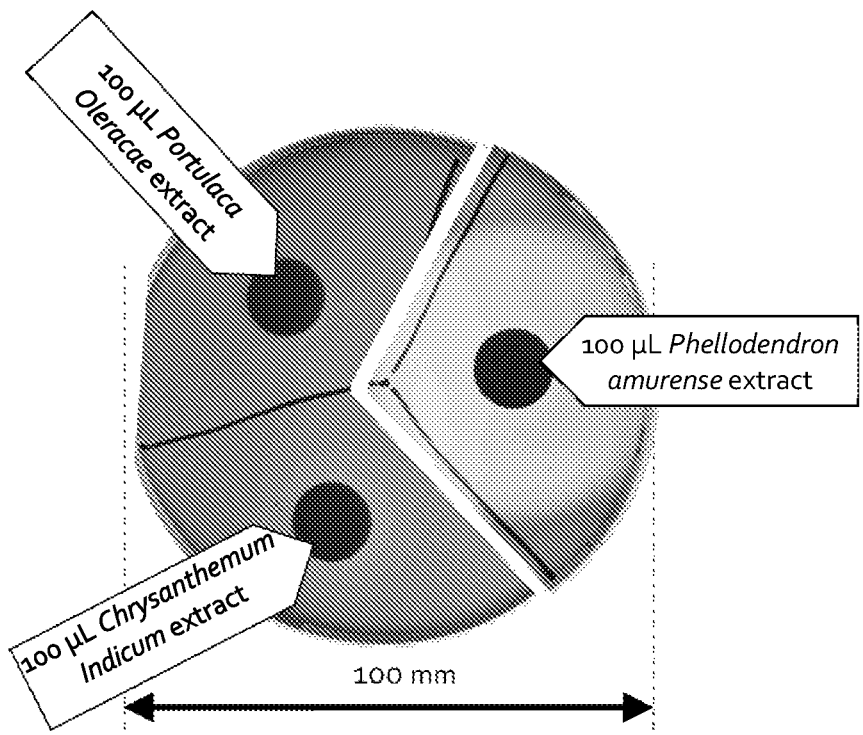
FIG. 5 presents the results of an agar-plate pathogen inhibition experiment.

Antibiotic activities of herbal extracts against Propionibacterium acnes were measured using Agar diffusion (FIG. 5) and Microplate dilution assays. Four out of six herbs exhibited antibiotic activity at different levels in at least one of the two assays. It is noted, as presented in Table 1, that the results for these two assays are not in full correlation; this is expected since antibiotic substances can only be effective in the agar diffusion assay if they have diffusion coefficients high enough to allow them to permeate the agar at adequate rates.

TABLE 1

Antibiotic effects of herbal extracts on Propionibacterium acnes.

| Herbal extract | Agar diffusion assay Inhibition zone diameter (mm) | Microplate dilution assay Minimum inhibitory concentration MIC (%) |
|---|---|---|
| Scutellaria baicalensis | 26 | 0.1 |
| Phellodendron amurense | 63 | 0.8 |
| Rheum palmatum | 31 | 0.9 |
| Sanguisorba officinalis | 28 | 1.3 |
| Portulaca oleracea | 0 | 25 |
| Chrysanthemum indicum | 0 | 12.5 |

Prebiotic Activities of Herbal Extracts

Figure 6:
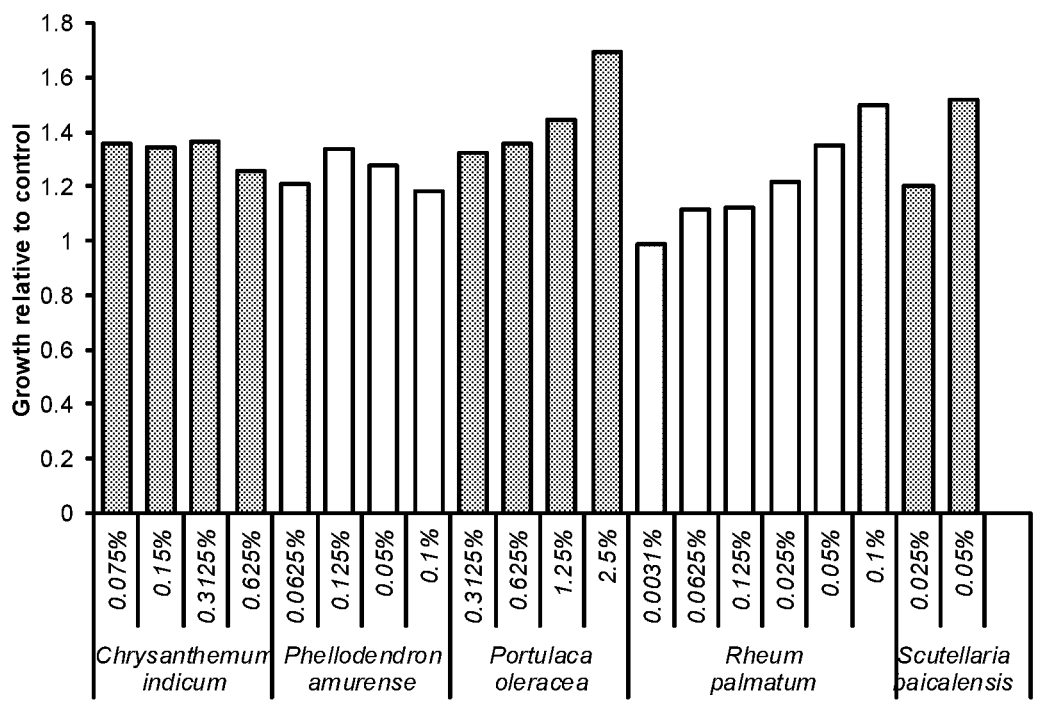
FIGS. 6 and 9 present the growth of *Staphylococcus epidermidis* under different treatments, showing the prebiotic features of the herbal extracts.

FIG. 6 illustrates that five of the herbal extracts show substantial prebiotic activity towards Staphylococcus epidermidis, i.e., the growth of Staphylococcus epidermidis is promoted due to the administration of the herbal extracts. The relative growth rates presented in FIG. 6 were calculated from the increase in 600 nm absorbance ($\Delta A_{600}$) over 18 hours, normalized against the increase shown by the control (average control $\Delta A_{600}$=0.35, pooled stdev between sets of triplicates=0.05).

Prebiotic and Antibiotic Effects of the Same Herbal Extract Dose

Figure 7:
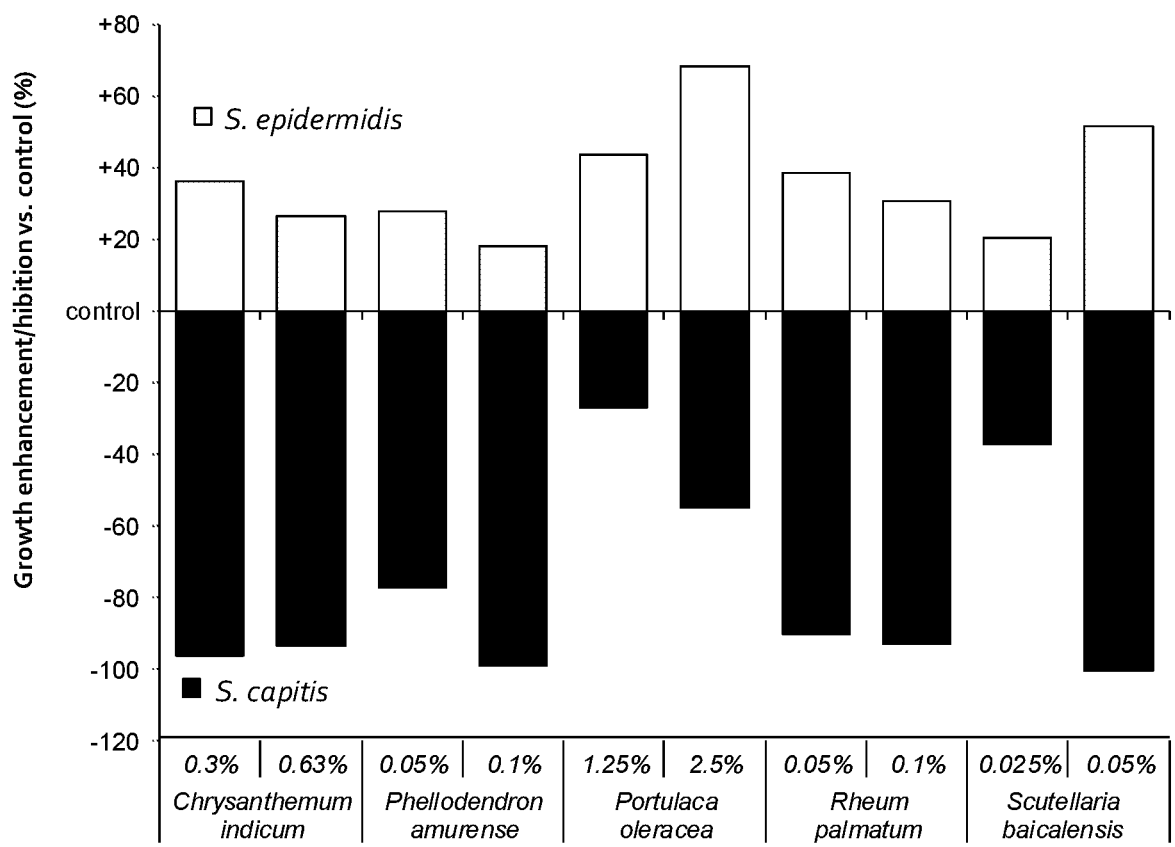
FIGS. 7 and 8 present the activity of various herbal extracts in promoting or inhibiting the growth of *Staphylococcus epidermidis* or *Staphylococcus capitis*, respectively.

FIG. 7 summarises the results of an experiment where five herbal extracts were added at the same concentrations to cultures of both S. epidermidis and S. capitis. All the herbal extract doses represented in FIG. 7 reduced growth of pathogen S. capitis and boosted the growth of S. epidermidis. Consequently, when employed for skin treatment, the five herbal extracts are proposed to be dually active, prebiotic and antibiotic, thus providing twofold benefit.

Figure 8:
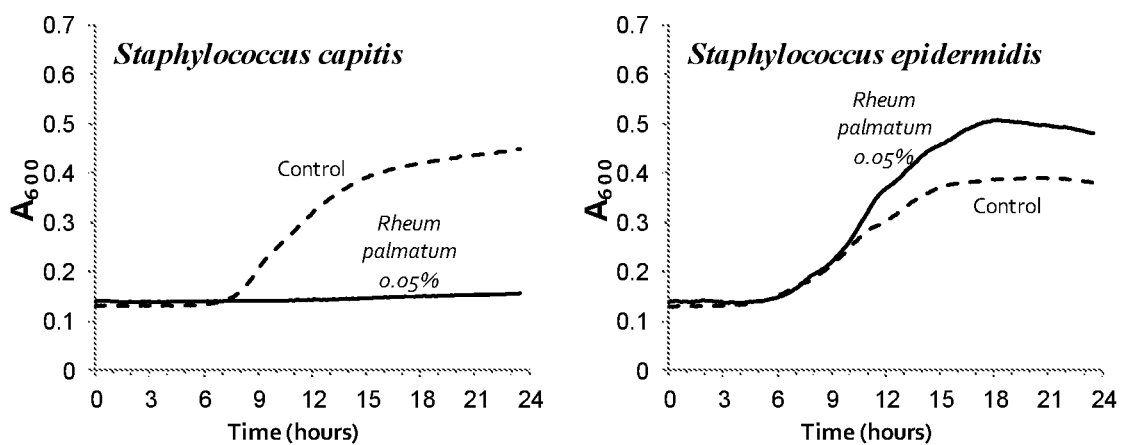

FIG. 8 further illustrates the contrasting effects of one of the extracts, i.e., Rheum palmatum, on the growth dynamics of two species of bacteria, wherein the same dose of the extract was used (0.05% Rheum palmatum root extract). As shown in FIG. 8, the 0.05% Rheum palmatum root extract inhibits the growth of Staphylococcus capitis (left panel) while promoting the growth of Staphylococcus epidermidis (right panel).

Figure 9:
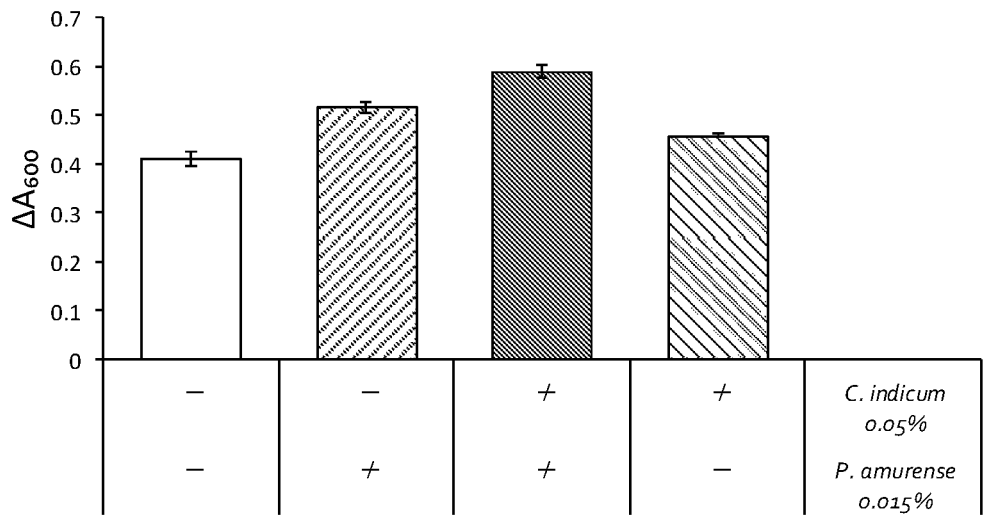

The prebiotic effects of certain herbal extracts may in some cases be complementary or even synergistic. The histograms in FIG. 9 represents the increase in 600 nm absorbance due to bacterial growth over 23 hours, presenting that while extracts of Phellodendron amurense and Chrysanthemum indicum both show prebiotic activity towards S. epidermidis, superior growth promotion may be achieved using the two extracts in combination.

Summary

Herbal extracts described in the invention exhibit prominent antibiotic activity against acne pathogens: Propionibacterium acne and Staphylococcus capitis. Prebiotic activity enhancing growth of Staphylococcus epidermidis is observed in five extracts. These findings are summarized in the table below.

| | Bacterium | | |
|---|---|---|---|
| Herbal extract | Propionibacterium acne | Staphylococcus capitis | Staphylococcus epidermidis |
| Chrysanthemum indicum | No activity | Inhibits growth | Promotes growth |
| Phellodendron amurense | Inhibits growth | Inhibits growth | Promotes growth |
| Portulaca oleracea | No activity | Inhibits growth | Promotes growth |
| Rheum palmatum | Inhibits growth | Inhibits growth | Promotes growth |
| Sanguisorba officinalis | Inhibits growth | No activity | No activity |
| Scutellaria baicalensis | Inhibits growth | Inhibits growth | Promotes growth |

Novel Findings:

for five of the six tested extracts, doses were found that promote the growth of beneficial bacteria while simultaneously inhibiting the growth of pathogenic bacteria. At least two extracts showed complementary or synergistic prebiotic activity.

Example 3

TABLE 2

Formulation for treating acne (gel)

| INCI Name | Reason for Use |
|---|---|
| Water | Solvent |
| Glycerin | Humectant |
| SD Alcohol | Solvent |
| Propanediol | Skin conditioner |
| Water | Skin conditioner |
| Capryloyl Glycine | |
| Hexylene Glycol | |
| Sarcosine | |
| *Cinnamomum zeylanicum* bark extract | |
| *Phellodendron amurense* bark extract | Skin conditioner |
| *Sanguisorba officinalis* root extract | Skin conditioner |
| Salicylic Acid | Keratolytic |
| Triethanolamine | pH control |
| *Chrysanthemum indicum* flower extract | Skin conditioner |
| *Portulaca oleracea* extract | Skin conditioner |
| *Rheum palmatum* root extract | Skin conditioner |
| Acrylates/C10-30 Alkyl Acrylate Crosspolymer | Viscosity controlling |
| *Scutellaria baicalensis* root extract | Skin conditioner |
| Xanthan Gum | Thickening agent |
| *Picea abies* Extract | Skin conditioner |
| Propanediol | |
| Benzyl Alcohol | Preservative |
| Sodium Phytate | Chelating agent |
| Water | |
| Alcohol | |
| Chlorphenesin | Preservative |
| Fragrance | Fragrance |

Example 4

Randomized Controlled Study of a Botanical Acne Spot Treatment

Objective:

The study evaluated the tolerability and efficacy of a new presented treatment for acne. The product is an OTC topical gel consisting of 2% salicylic acid (SA), which is also enriched in botanicals that have been shown to have anti-inflammatory properties.

Design:

The study was designed as a single-site, randomized, investigator-blinded, split-face 10 day study Setting:

Subjects enrolled with a minimum of 2 inflammatory papular acne lesions and 2 non-inflammatory open or closed comedones on both sides of the face in symmetrical locations, to the greatest degree possible. One side of each subject's face was randomly selected to receive the study treatment product.

Participants:

25 subjects, 15 female and 10 males, ages 12 to 43 years, suffering from mild to moderate acne.

Measurements:

Study duration was 10 days, with study visits occurring at baseline (Day 0), Day 1, Day 2, Day 3, Day 7 and Day 10. Subjects underwent investigator facial evaluation and lesion assessment by dermatologist at each of the visit days. For the inflammatory lesions, the assessed parameters were erythema, elevation, induration and overall impression. The assessed non-inflammatory parameters were elevation and overall impression.

Results:

The observed difference between the treatment and the control group increased between day 1 and day 2 and reached an average of 15% to 20% with small varieties between the parameters and stayed similar across the remaining visits. Statistically significance (p<0.005) was achieved for all inflammatory and non-inflammatory tested parameters.

Conclusion:

This study was performed to determine the safety, efficacy and ease of use of a botanical acne treatment gel in providing a reduction in inflammatory acne lesion erythema, elevation and induration. Erythema and elevation were the most influential parameters in inflammatory lesion with improvement noted after 2 days of application.

Methods 25 subjects, 15 female and 10 males, ages 12 to 43 years, with mild to moderate acne were recruited and qualified for the study. The study was designed as a single-site, investigator-blinded, split-face 10 day study (Dermatology Consulting Services, PLLC, High Point, N.C., USA). The study was conducted under Institutional Review Board (Concordia IRB, Beach Haven, N.J., USA), a signed informed consent form and a photographic release form were obtained from each subject prior to performing any study procedure.

Subjects enrolled according to the inclusion criteria with a minimum of 2 inflammatory papular acne lesions and 2 non-inflammatory open or closed comedones on both sides of the face in symmetrical locations, to the greatest degree possible. Subjects did not use any topical acne treatments for 2 weeks prior to study entry, did not take any oral acne medications for 4 weeks prior to study entry, and did not use any topical acne medications for 2 weeks prior to study entry.

In the study, one side of each subject's face was randomly selected to receive the study treatment product—Kamedis Acne Spot Treatment. The treatment selected side of the face was washed pre-treatment by Dove sensitive skin unscented soap bar and was treated by Kamedis spot treatment. Subjects were requested to apply the treatment product three times daily following face wash with the Dove bar, as per instructions, morning noon and evening. The non-treated face side or the control side was washed by the Dove bar three times daily, as the treatment side, however was not treated with a topical product.

The study duration was 10 days, with study visits occurring at baseline (Day 0), Day 1, Day 2, Day 3, Day 7 and Day 10. Subjects underwent investigator facial evaluation and lesion assessment by dermatologist at each of the visit days. Digital photos were taken of the face at Day 0, Day 1, Day 2, Day 3, and Day 10. Images were taken 90 degrees, +45 degrees, and −45 degrees to the subject with a Nikon D-90 camera in a Canfield 3-point head mount with an IntelliFlash system and a consistent f-stop for reproducibility at all time points.

The investigator assessed each inflammatory and non-inflammatory lesion on each side of the face separately for a number of parameters at each of the visit days 0, 1, 2, 3, 7 and 10. For the inflammatory lesions, the assessed parameters were erythema, elevation, induration and overall impression. As for the non-inflammatory, the assessed parameters were elevation and overall impression. Per each parameter, the following grading scale was used: 0=None, 1=Minimal, 2=Mild, 3=Moderate and 4=Severe.

Following the treatment, on day 10, the subjects completed a sponsor supplied marketing questionnaire and also provided their comments for the entire experience. The statistical analysis used a two-way analysis of variance (ANOVA) with visit and treatment/control as main factors and the interaction between them. A significant interaction would mean that the difference between the treatment and the control is not similar across visits. Factors with P-Values smaller than 0.05 are considered as statistically significant. For each parameter, the original scores have been transformed to percentage of improvement by calculating the percentage of increased score comparing to the score measurement of each patient at baseline (Day 0).

Results

Out of the 25 subjects enrolled, 24 subjects completed the study. One subject did not complete the study due to personal reasons unrelated to the tested product. No adverse experiences or events occurred during the course of the trial.

Demographic characteristics of the subjects are presented (see Table 3 below). No significant statistical difference was observed in characteristics between the randomly selected treatment and control lesion groups in the baseline visit (Day 0).

TABLE 3

Subject demographic characteristics

| Gender | N | Age range | Median Age (mid quartile) | Race | |
|---|---|---|---|---|---|
| | | | | Caucasian | African American |
| F | 15 | 13-43 | 23 (17.5-32) | N = 11 | N = 4 |
| M | 10 | 12-22 | 16 (15.25-18.25) | N = 9 | N = 1 |
| Total: | 25 | 12-43 | 19 (16-24) | N = 20 | N = 5 |

The investigator assessed at each visit the subject inflammatory chosen lesions for erythema (FIG. 10), elevation (FIG. 11), induration and overall impression (FIG. 12) and the non-inflammatory lesions for elevation and overall impression.

In general, it can be seen that the Kamedis Acne Spot Treatment demonstrated a consistent improvement over the control group across time. Improvement is observed after one day of treatment and continues to expand over the control after the following day (day 2). Kamedis Acne Spot Treatment maintains its advantage during the course of the following visits up to day 10. The observed difference between the treatment and the control group increases between day 1 and day 2 and reaches an average of 15% to 20% with small varieties between the parameters and usually stays similar across the remaining visits. Statistically significance ($p<0.005$) was achieved for all inflammatory and non-inflammatory parameters tested.

Figure 10:
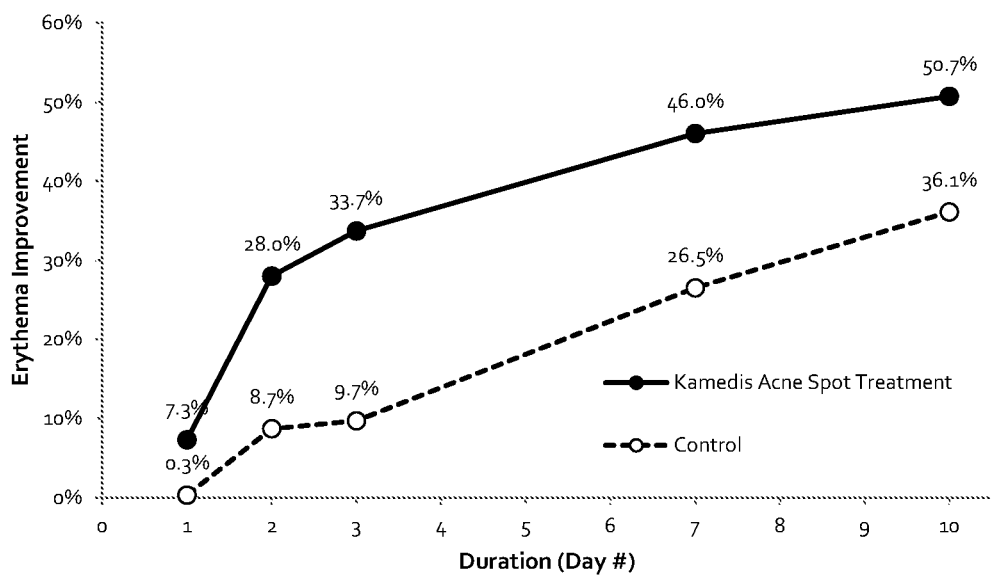
FIGS. 10, 11 and 12 present the erythema (FIG. 10), elevation (FIG. 11) and overall impression (FIG. 12) of the subject inflammatory lesions.

The erythema improvement measured on inflammatory lesions reached around 20% difference between the tested product and the control after 2 days and achieved the maximum difference of 24% on day 3. The erythema improvement magnitude of the tested product reached 50% after 10 treatment days, keeping a similar difference between the tested product and the control (FIG. 10).

Figure 11:
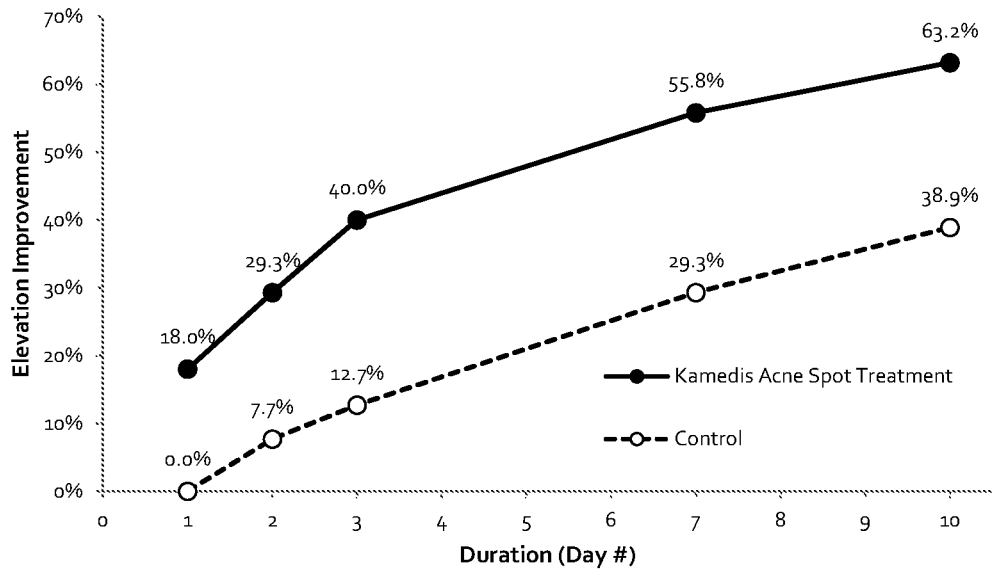

The elevation improvement measured on the inflammatory lesions only, reached 18% of improvement on the first day, this was also the difference compared to the control, since the control value showed 0% on the first day. On the second day the difference was over 20% and remained similar or increased until day 10. The elevation-improvement magnitude of the tested product reached 63% on day 10 (FIG. 11).

The induration improvement on inflammatory lesions showed smaller difference compared to the two previous parameters. On day 2 the difference between the test product and the control reached 10% and increased to 20% on day 3, remaining similar for the rest of the study. The induration improvement magnitude of the tested product reached 52% by day 10.

Figure 12:
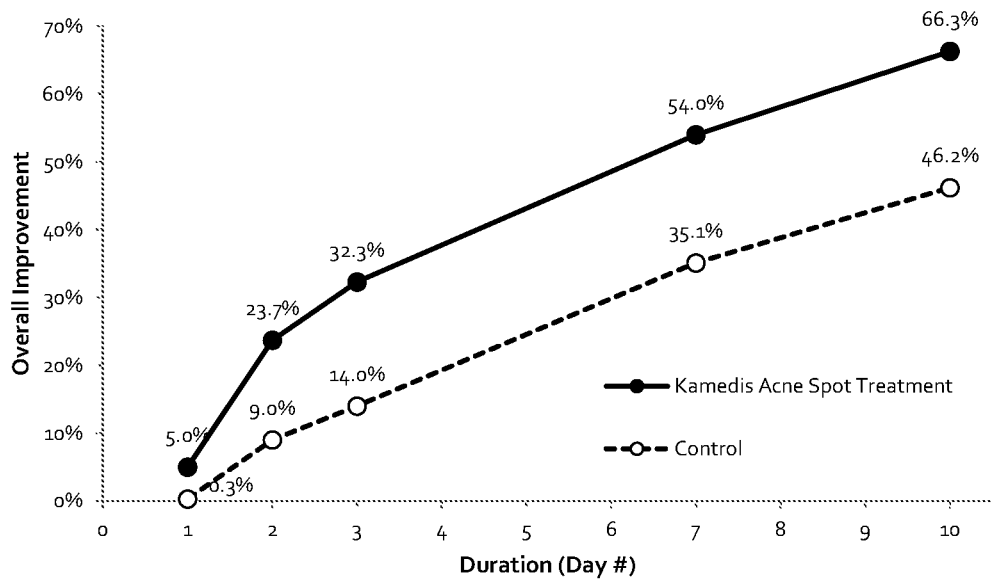

The overall impression of the inflammatory lesions of the tested product reached 66% by day 10, maintaining a 20% improvement over the control starting from days 2 and 3 (FIG. 12).

The elevation improvement of the tested product that was tested on the non-inflammatory lesions showed lesser improvement by day 10 (31%) compared to the inflammatory lesions. The difference between the tested product and the control was also smaller, starting at 5% on day 2 and increasing to 13% on days 7 and 10.

The overall improvement of the non-inflammatory lesions was very similar to the elevation results, starting with 7% difference between the tested product and the control on day 2 and reaching 13% difference on day 10, with 31% as final e improvement of the tested product by day 10.

Figure 13A:
FIG. 13 presents appearance of acne pimple before (a) and after (b) treatment.
Figure 13B:
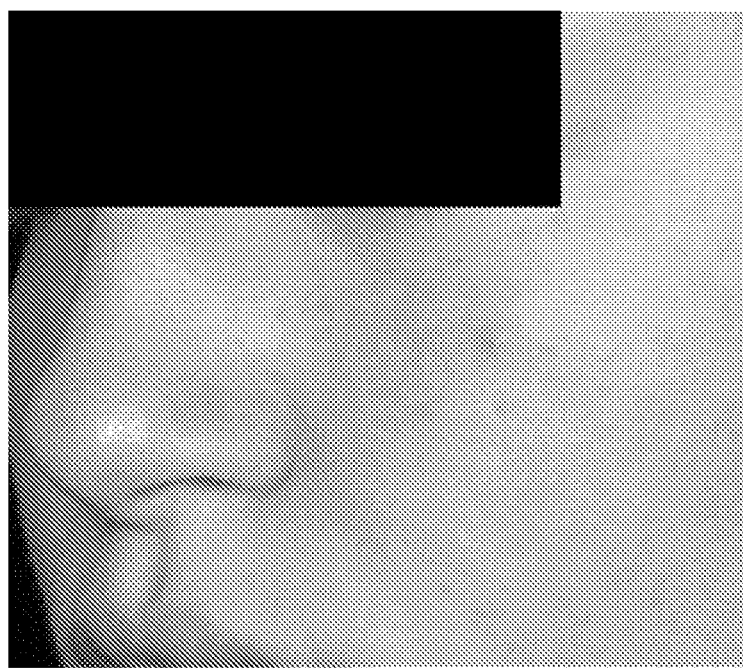

In addition to the measured parameters, clear improvement was visually evident as early as in day 2 or 5 applications of the treatment product (FIGS. 13a and 13b).

Discussion

The presented study evaluated a new botanically-based acne treatment with anti-inflammatory activity. The product was found to be effective and well tolerated in improving acne symptoms. The control side included a general wash by a soap, but did not include a topical treatment for the inflammatory and non-inflammatory acne lesions. The choice of a suitable control is a challenge in acne studies because healing occurs without intervention. On inflammatory lesions, the acne study botanical product offered better results over time, usually after two days, with the exception of elevation for which significant improvement is evident after one day of treatment. On non-inflammatory lesions, the acne study botanical product was also beneficial versus the control, although to a lesser extant than for the inflammatory lesions.

The acne study investigated a product that was based on 11.5% herbal botanical ingredients with anti-inflammatory and anti-bacterial activity, such as *Rheum palmatum, Portulaca oleracea, Chrysanthemum indicum, Scutellaria baicalensis, Phellodendron amurense* and *Sanguisorba officinalis*. The *Rheum palmatum* and *Scutellaria baicalensis* also show anti-oxidative activity as well as reduction in sebum secretion, which may assist in improving and relieving the severity of acne lesions. The botanicals were selected due to their anti-inflammatory properties. They were selected among numerous herbs based on a thorough literature review that was followed by in vitro studies on keratinocyte cell line and on skin models. The in vitro tests studied the anti-inflammatory activity of the botanicals by inhibition of TNF-alpha release, and yielded promising results in the combination of the above herbs. The chemically-active molecules that are connected with the anti-inflammatory activity of the *Rheum palmatum* include emodin and aloe-emodin. Both are produced by *Rheum palmatum* and are effective and selective as inhibitors of the enzyme 11β-HSD1 that catalyzes the conversion of the stress hormone cortisol to the inactive metabolite cortisone. Moreover, there is recent scientific evidence supporting the use of emodin in medicine for the treatment of various inflammatory diseases through the regulation of inflammasome activation, where emodin was shown to attenuate NLRP3 inflammasome activation leading to decreased secretion of cleaved IL-1β and blocking of the inflammasome-induced pyroptosis.

This study is a preliminary study presenting this original botanically-based product, and therefore included only a small sample size.

SUMMARY

This study was performed to determine the safety, efficacy and ease of use of a botanical acne treatment gel in alleviating inflammatory acne lesion erythema, elevation and induration. Erythema and elevation were the most influenced inflammatory-lesion parameters, with improvement noted after 2 days of application.

What is claimed is:

1. A topical formulation comprising an herbal extract of *Phellodendron amurense* bark and at least one of *Sanguisorba officinalis* root extract and *Chrysanthemum indicum* flower extract; and/or active molecules therefrom, in an amount effective for treating or preventing acne, in a cosmetically and/or dermatologically acceptable excipient for topical administration,
wherein the herbal extract is an aqueous extract that is purified by chromatography and/or by using a macroporous resin and configured to provide prebiotic activity that promotes growth of *Staphylococcus epidermidis*.

2. The topical formulation according to claim 1, further comprising at least one of the herbal extracts: *Portulaca oleracea* extract, *Rheum palmatum* root extract, and *Scutellaria baicalensis* root extract.

3. The topical formulation according to claim 2, further configured to provide at least one of: anti-inflammatory activity, anti-microbial activity, and anti-oxidant activity.

4. The topical formulation according to claim 1, further configured to provide antibiotic activity that selectively inhibits growth of *Staphylococcus capitis* and/or *Cutibacterium (Propriobacterium) acnes*.

5. The topical formulation according to claim 1, further comprising at least one of: an anti-inflammatory compound, anti-microbial agent, prebiotic ingredient, skin hydration enhancing ingredient, analgesic agent, anti-oxidant, a sebum regulator, a keratolytic agent or any combination thereof.

6. The topical formulation according to claim 1, further comprising salicylic acid.

7. The topical formulation according to claim 6, wherein the salicylic acid is present in the formulation in a range of 0.1-5.0% w/w.

8. The topical formulation according to claim 1, wherein the topical formulation is a gel.

9. The topical formulation according to claim 1, having a pH in a range of 4.0-5.5.

10. The topical formulation according to claim 2, wherein a combined concentration of the herbal extracts in the formulation is at least 1% w/w.

11. The topical formulation according to claim 2, wherein a combined concentration of *Chrysanthemum indicum, Portulaca oleracea, Rheum palmatum*, and *Scutellaria baicalensis* in the formulation is about 5.5% w/w, a concentration of *Sanguisorba officinalis* in the formulation is about 3% w/w, and a concentration of *Phellodendron amurense* in the formulation is about 3% w/w, wherein the term "about" refers to ±10% of the concentration.

12. A method of treating acne the method comprising applying a topical formulation comprising the herbal extracts *Phellodendron amurense* bark extract and at least one of *Sanguisorba officinalis* root extract and *Chrysanthemum indicum* flower extract; or their active molecules, in a cosmetically and/or dermatologically acceptable excipient for topical administration, to a subject in need for treating or preventing, wherein the herbal extract is an aqueous extract that is purified by chromatography and/or by using a macroporous resin and wherein the formulation provides prebiotic activity that promotes growth of *Staphylococcus epidermidis*.

13. The method of claim 12, further comprising applying in the topical formulation at least one of: *Portulaca oleracea* extract, *Rheum palmatum* root extract, *Scutellaria baicalensis* root extract, *Cinnamomum zeylanicum* bark extract, *Picea abies* extract, glycerin, and any combination thereof.

14. The method of claim 12, wherein at least one of the extracts further provides at least one of: anti-inflammatory activity, anti-microbial activity, and anti-oxidant activity.

15. The method of claim 12, wherein at least one of the extracts further provides antibiotic effects inhibiting growth of *Staphylococcus capitis* and/or of *Cutibacterium (Propriobacterium) acnes*.

16. The method of claim 12, wherein the topical formulation further comprises an agent or agents providing at least one of: anti-inflammatory activity, anti-microbial activity, skin hydration-enhancing activity, analgesic activity, anti-oxidative activity, sebum regulation and keratolytic activity.

17. The method of claim 12, wherein the topical formulation further comprises salicylic acid in a range of 0.1-5.0% w/w in the formulation.

18. A topical formulation comprising herbal extracts of *Phellodendron amurense* bark, *Sanguisorba officinalis* root extract, *Portulaca oleracea* extract, *Rheum palmatum* root extract, *Chrysanthemum indicum* flower extract and *Scutellaria baicalensis* root extract; and/or active molecules therefrom, in an amount effective for treating or preventing acne, in a cosmetically and or dermatologically acceptable excipient for topical administration,
wherein the herbal extract is an aqueous extract that is purified by chromatography and/or by using a macroporous resin and configured to provide prebiotic activity that promotes growth of *Staphylococcus epidermidis*.

19. The topical formulation of claim 1, wherein the herbal extract comprises *Phellodendron amurense* bark and *Chrysanthemum indicum* flower extract; and/or active molecules therefrom, in an amount effective for treating or preventing acne, in a cosmetically and or dermatologically acceptable excipient for topical administration, wherein the herbal extract is an aqueous extract that is purified by chromatography and/or by using a macroporous resin.

20. A topical formulation comprising an herbal extract of *Phellodendron amurense* bark and *Chrysanthemum indicum* flower extract; and/or active molecules therefrom, in an amount effective for treating or preventing acne, in a cosmetically and or dermatologically acceptable excipient for topical administration, wherein the herbal extract is an aqueous extract that is purified by chromatography and/or by using a macroporous resin and configured to provide prebiotic activity that promotes growth of *Staphylococcus epidermidis*.

* * * * *